(12) United States Patent
Narayan et al.

(10) Patent No.: US 8,765,140 B2
(45) Date of Patent: *Jul. 1, 2014

(54) DNA VACCINE COMPOSITIONS WITH HIV/SIV GENE MODIFICATIONS

(75) Inventors: Opendra Narayan, Lenexa, KS (US); Zhenqian Liu, Lenexa, KS (US)

(73) Assignee: University of Kansas Medical Center, Kansas City, KS (US)

( * ) Notice: Subject to any disclaimer, the term of this patent is extended or adjusted under 35 U.S.C. 154(b) by 366 days.

This patent is subject to a terminal disclaimer.

(21) Appl. No.: 13/185,148

(22) Filed: Jul. 18, 2011

(65) Prior Publication Data

US 2012/0020999 A1     Jan. 26, 2012

Related U.S. Application Data

(63) Continuation of application No. 10/941,164, filed on Sep. 15, 2004, now Pat. No. 7,488,485.

(60) Provisional application No. 60/503,194, filed on Sep. 15, 2003.

(51) Int. Cl.
    *A61K 39/21*          (2006.01)
    *A61K 39/12*          (2006.01)
    *C07H 21/04*         (2006.01)

(52) U.S. Cl.
    USPC ............... 424/208.1; 424/204.1; 536/23.72; 536/24.1

(58) Field of Classification Search
    USPC ............... 424/204.1, 208.1; 536/23.72, 24.1
    See application file for complete search history.

(56) References Cited

U.S. PATENT DOCUMENTS 7,488,485 B2 *    2/2009    Narayan et al. ............ 424/208.1
8,003,113 B2 *    8/2011    Narayan et al. ............ 424/208.1

* cited by examiner

*Primary Examiner* — Shin-Lin Chen
(74) *Attorney, Agent, or Firm* — Kimberly A. Honeycutt; Polsinelli PC

(57) ABSTRACT

The present invention is directed to a DNA vaccine for immunization against HIV. The invention comprises a DNA molecule that has a sequence encoding a plurality of viral proteins capable of stimulating an immune response against HIV. The DNA molecule is rendered safe for use as a vaccine by the disruption of genes encoding reverse transcriptase, integrase, and Vif. The DNA molecule is further rendered safe by at least a partial deletion of the 3' LTR.

10 Claims, 2 Drawing Sheets

SEQUENCE LISTING

```
<160> NUMBER OF SEQ ID NOS: 7

<210> SEQ ID NO 1
<211> LENGTH: 9994
<212> TYPE: DNA
<213> ORGANISM: Artificial Sequence
<220> FEATURE:
<223> OTHER INFORMATION: Simian immunodeficiency virus/human
      immunodeficiency virus

<400> SEQUENCE: 1
tggaagggat ttattacagt gcaagaagac atagaatctt agacatgtac ttagaaaagg      60
aaaaaggcat cataccagat tggcaggatt acacctcagg accaggaatt agatacccaa     120
agacatttgg ctggctatgg aaattagtcc ctgtaaatgt atcagatgag gcacaggagg     180
atgaagagca ttatttaatg catccagctc aaacttccca gtgggatgac ccttggagag     240
aggttctagc atggaagttt gatccaactc tggcctacac ttatgaggca tatgttagat     300
acccagaaga gtttggaagc aagtcaggcc tgtcagagga agaggttaaa agaaggctaa     360
ccgcaagagg ccttcttaac atggctgaca agaaggaaac tcgctgaaac agcagggact     420
ttccacaagg ggatgttacg gggaggtact ggggaggagc cggtcgggaa cgcccacttt     480
cttgatgtat aaatatcact gcatttcgct ctgtattcag tcgctctgcg gagaggctgg     540
caggttgagc cctgggaggt tctctccagc actagcaggt agagcctggg tgttccctgc     600
tagactctca ccagcacttg gccggtgctg ggcagagtga ttccacgctt gcttgcttaa     660
agccctcttc aataaagctg ccattttaga agtaagctag tgtgtgttcc catctctcct     720
agccgccgcc tggtcaactc ggtactcaat aataagaaga ccctggtctg ttaggaccct     780
ttctgctttg ggaaaccgaa gcaggaaaat ccctagcaga ttggcgcccg aacagggacg     840
cgaaagcgaa agtagaacca gaggagctct ctcgacgcag gactcggctt gctgaagcgc     900
gcacggcaag aggcgagggg cggcgactgg tgagtacgcc attttttgact agcggaggct     960 agaaggagag agatgggtgc gagagcgtca atattaagcg ggggacaatt agatagatgg    1020
```

-continued

```
gaaaaaattc ggttacggcc aggggggaaag aaaagatata agttaaaaca tatagtatgg    1080
gcaagcagag agctagaacg attcgcagtt aaccctggcc tgttagaaaac agcagaaggc    1140
tgtagacaaa tactgggaca gctacaacca tcccttcaga caggatcaga ggaacttaaa    1200
tcattattta atacaatagc taccctctat tgtgtacatc aaagaataga gataaaagac    1260
accaaggaag ctttagataa gatagaggaa gagcaaaaca aaagtaagaa aaaagcacag    1320
caagcagcag ctgacacagg aaacagcagc agccaagtca gccaaaatta ccctatagtg    1380
cagaacgctc agggacaaat ggtacatcag gccatatcac ctagaacttt aaatgcatgg    1440
gtaaaagtag tagaagaaaa ggcttttaac ccagaagtaa tacccatgtt tgcagcattg    1500
tcagaaggag ccacccccaca agatttaaac accatgctaa acacagtggg gggacatcaa    1560
gcagccatgc aaatattaaa agagactatc aatgaggaag ctgcagaatg ggatagattg    1620
catccagtac atgcagggcc tattgcacca ggccaaatga gagaaccaag gggaagtgac    1680
atagcaggaa ctactagtac ccttcaggaa caaataggat ggatgacaaa taatccacct    1740
atcccagtag gagaaatcta taaaaaatgg ataatcatgg gattaaataa aattgtaagg    1800
atgtatagcc ctaccagtat tctggacata agacaaggac caaaggaacc ctttagagac    1860
tatgtagacc ggttctataa aactctaaga gccgagcaag cttcacagga agtaaaaaat    1920
tggatgacag aaaccttgtt ggtccaaaat tcaaacccg attgtaagac tattttaaaa    1980
gcattaggac caggagctac actagaagaa atgatgacag catgccaggg agtgggagga    2040
cctggccata aagcaagagt tttggcagaa gcaatgagcc aagtaacaaa tccaacggcc    2100
gtgatgatgc agaaaagcaa ttttaggggc caaagaaaaa ttgttaagtg ttttaattgt    2160
ggcaaagaag ggcacatagc caaaaattgc agggctccta gaaaaaaggg ctgttggaaa    2220
tgtggaaagg aaggacacca aatgaaagat tgtactgaaa gacaggctaa ttttttaggg    2280
aagatctggc cttcctacaa gggaaggcca gggaattttc tcaaagcag gctagaacca    2340
acagccccac cagaagcgag cttcaggttt ggggaggaga caacaactcc ccctcagaag    2400
caggagacga tagacaagga ggtgtatcct ttaacctccc tcagatcact ctttggcaac    2460
gaccccctcgt cacaataaag ataggggggc aactaaaaga agctctatta gatacaggag    2520
cagatgatac agtgttagaa gacatgaatt tgccaggaaa atggaaacca aaaatgatag    2580
ggggaattgg aggatttatc aaagtaaaac agtatgatca gatacccata gaaatctgtg    2640
gacataaaac tataggtaca gtattaatag gacctacacc tgtcaacata attggaagga    2700
atttgttgac tcagcttggt tgcactttaa attttcccat tagtcctatt gaaactgtac    2760
cagtaaaatt aaagccagga atggatggcc caaaagttaa gcaatggcca ttgacagaag    2820
aaaaaataaa agcattaatg gagatatgca cagaaatgga aaaggaaggg aaaatttcaa    2880
aaattgggcc tgaaaatcca tacaatactc cagtgtttgc cataaagaaa aaagacagta    2940
ctaagtggag aaaattagta gatttcagag aacttaataa gaaaactcaa gacttctggg    3000
aggttcaatt aggaatacca catcccgcgg ggttaaaaaa gaaaaagtca gtaacagtac    3060
tggatgtggg tgatgcatac ttctcagttc ccttagatga agattttagg aagtatactg    3120
catttaccat acctagtata aacaatgaga catcaggaat tagatatcag tacaatgtgc    3180
ttccacaggg atggaaaggg tcaccatgtc agatcccagg gagagaatcc cacctggaaa    3240
cagtggagaa gagacaatag gagaggcctt cgaatggcta aacagaacag tagaggagat    3300
aaacagagag gcggtaaacc acctaccaag ggagctaatt ttccaggttt ggcaaaggtc    3360
```

```
ttgggaatac tggcatgatg aacaagggat gtcaccaagc tatgtaaaat acagatactt   3420
gtgtttaata caaaaggctt tatttatgca ttgcaagaaa ggctgtagat gtctagggga   3480
aggacatggg gcaggggat ggagaccagg acctcctcct cctcccctc caggactagc    3540 ataaatggaa gaaagacctc cagaaaatga aggaccacaa agggaaccat gggatgaatg   3600
ggtagtggag gttttggaag aactgaaaga agaagcttta aaacattttg atcctcgctt   3660
gctaactgcc cttggtaatc atatctataa tcgtcacgga gacactctag agggagcagg   3720
agaactcatt agaatcctcc aacgagcgct cttcatgcat ttcagaggcg gatgcatcca   3780
ctccagaatc ggccaacctg agggaggaaa tcctctctca gctataccgc cctctagaag   3840
cattctgtag agcaagaaat ggagccagta gatcctagac tagagccctg gaagcatcca   3900
ggaagtaagc ctaaaactgc ttgtaccaat tgctattgta aaaagtgttg ctttcattgc   3960
caagtttgtt tcataacaaa agccttaggc atctcctatg gcaggaagaa gcggagacag   4020
cgacgaagag ctcatcagaa cagtcagact catcaagctt ctctatcaaa gcagtaagta   4080
gtacatgtaa tgcaacctat accaatagta gcaatagtag cattagtagt agcaataata   4140
atagcaatag ttgtgtggtc catagtaatc atagaatata ggaaaatatt aagacaaaga   4200
aaaatagaca ggttaattga tagactaata gaaagagcag aagacagtgg caatgagagt   4260
gaaggagaga tatcagaatt atcagcactt gtggagagag ggcatcttgc tccttgggat   4320
attaatgata tgtagcactg caggacaatt gtgggtcaca gtctattatg gggtacctgt   4380
gtggagagaa gcaaccacca ctctattttg tgcatcagat gctaaagcat atgatacaga   4440
ggtgcataat gtctgggcca cacatgcctg tgtacccaca gaccccagcc cacaagaaat   4500
ggcattggaa aatgtgacag aaaattttga catgtggaaa ataatatgg tagaacagat    4560 gcatgaagat ataatcagct tatgggatca aagcctaaag ccttgtgtaa aattaactcc   4620
actatgtgtt actttaaatt gcactgatgt aaagagaaat gctactagta acactagtag   4680
tagctgggaa aggatggaac caggagaaat aaaaaactgc tctttcaatg tcacctcaaa   4740
tataagagat aagatgcgga aagaatatgc actctttat aaacttgatg taataccaat    4800
aaataatact agtgataata gtgctaaata tagattgata agttgtaaca cctcagtcct   4860
tacacaagct tgtccaaaaa tatcctttga gccaattcca atacattatt gtaccccggc   4920
tggttttgcg cttctgaagt gtaatgataa ggagttcaat ggaacgggac catgtaaaaa   4980
tgtcagcaca gtacaatgta cacatggaat caagccagta gtatcaactc aactgctgtt   5040
aaatggcagt ctatcagaag gaggggttgt aattagatct caaaatttca caaacaatgc   5100
taaaaccata atagtacagc tgaatgaaac tgtagaaatt aattgtacaa ggcccaacaa   5160
caatacaaga gaagtataa atataggacc agggagagca ttttatgcag cagaacaaat   5220
aataggagat ataagacaag cacattgtaa cattagtaga gcaaaatgga ataacacttt   5280
aaaactgata gttggaaaat tacaagaaca atttgggaag aaaacaataa tctttaatca   5340
atcctcagga ggagaccctg agattgtaac acacagtttt aattgtggag gggaattttt   5400
ctactgtgat tcaacacaac tgtttaacag tacttggacg aatgaaaata cgggtccaa    5460 cactaaaggg aatgacacaa tcatactacc atgcagaata aaacaaattg taaacctgtg   5520
gcaggaagta ggaaaagcaa tgtatgcccc tcccatcaga agaccaatta gatgctcatc   5580
aaatattaca gggctgctac taacaagaga tggtggtcct aataggacga acgagacatt   5640
cagacctgga ggaggagata tgagggacaa ttggagaagt gaattataca aatataaagt   5700
agtaaaaatt gaaccattag gagtagcacc caccaaggca aagagaagag tggtgcaaag   5760
```

```
agaaaaaaga gcagtgggaa taggagctct gttccttggg ttcttgggaa cagcaggaag    5820
cactatgggc gcagcgtcac tgacgctgac ggtacaggcc agacaattat tgtctggtat    5880
agtgcaacag cagaacaatt tgctgagagc tattgaagcg caacaacatc tgttgcagct    5940
cacagtctgg ggcatcaagc agctccaggc aagagtcctg gctgtggaaa gatacctaag    6000
ggatcaacag ctcctgggaa tttggggttg ctctggaaaa ctcatttgca ccactgctgt    6060
gccttggaac actagttgga gtaataaatc tctagatgac atttggaaca acatgacttg    6120
gatgcagtgg gaaagagaaa ttgacaatta cacaaacaca atatacacct tacttcagga    6180
atcacaactc caacaagaac agaatgaaaa agaactattg gaattggata aatgggcaag    6240
tttgtggaat tggttcgata taacaagttg gctgtggtat ataaaaatat tcataatgat    6300
agtaggaggc ttgataggtt taagaatagt ttttactgta ctttctatag tgaatagagt    6360
taggaaggga tactcaccat tatcgttcca gacccaccgc ccagctccag ggggacccga    6420
caggcccgaa ggaatcgaag aagaaggtgg agagagagac agagaaagat ccaatcaatt    6480
agtggatgga ttcttagcaa ttatctgggt cgacctgcgg aacctgtgcc tcttcagcta    6540
ccaccgcttg agagacttac tcttgattgc aacgaggatt gtggaacttc tgggacgcag    6600
ggggtgggaa gccctcaaat attggtggaa tctcctgcag tattggagtc aggaactgaa    6660
gaatagtgct gttagcttgc ttaatgccat agccatagca gtagctgagg ggacagatag    6720
aattatagaa gtagtacaaa gggggttag agctgttctt aacatacca caagaataag      6780 acagggagcg gaaaggcttc ttgtataaga tgggtggcaa gttgtcaaaa gtaagatgc      6840 ctggatggtc tactataagg gaaagaatga gacgagctca gccagcagca gagccagcag    6900
cagttggggt gggagcagca tctcgagacc tggaaagaca tggagcactc acaagtagca    6960
atacagcagc taacaatgct gattgtgcct ggctagaagc acaagaggac gaggaagtgg    7020
gttttccagt cagacctcag gtacctctta ggccaatgac ttacaaggga gctgtagatc    7080
ttagccactt tttaaaagaa aagggggggac tggaagggtt agtttactcc caaaaaagac    7140 aagcatcct tgatctgtgg gtctaccaca cacaaggcta cttccctgat tggcagaact      7200
acacaccagg gccagggatc agatatcccc tgacctttgg atggtgcttc aagctagtac    7260
cagttgatcc agataaggta gaagaggcca atgaaggaga gaacaactgc ttattacacc    7320
ctatggccca gcatgggatg gatgacccag agaaagaagt gttagtgtgg aagtttgaca    7380
gccgcctagc atttcatcac atggcccgag agctgcatcc ggagtactac aaagactgct    7440
gagcggccgc cctgcaggtc gacctcgagg ggggcccgg taccttaatt aattaaggta      7500
ccaggtaagt gtacccaatt cgccctatag tgagtcgtat tacaattcac tcgatcgccc    7560
ttcccaacag ttgcgcagcc tgaatggcga atggagatcc aattttttaag tgtataatgt    7620 gttaaactac tgattctaat tgtttgtgta ttttagattc acagtcccaa ggctcatttc    7680
aggcccctca gtcctcacag tctgttcatg atcataatca gccataccac atttgtagag    7740
gttttacttg ctttaaaaaa cctcccacac ctcccctga acctgaaaca taaaatgaat      7800
gcaattgttg ttgttaactt gtttattgca gcttataatg gttacaaata aagcaatagc    7860
atcacaaatt tcacaaataa agcatttttt tcactgcatt ctagttgtgg tttgtccaaa    7920
ctcatcaatg tatcttaacg cgtaaattgt aagcgttaat gcttcacgac cacgctgatg    7980
agctttaccg cagctgcctc gcgcgtttcg gtgatgacgg tgaaacctc tgacacatgc      8040 agctcccgga gacggtcaca gcttgtctgt aagcggatgc cgggagcaga caagcccgtc    8100
```

| | |
|---|---|
| agggcgcgtc agcgggtgtt ggcgggtgtc ggggcgcagc catgacccag tcacgtagcg | 8160 |
| atagcggagt gtatactggc ttaactatgc ggcatcagag cagattgtac tgagagtgca | 8220 |
| ccatatatgc ggtgtgaaat accgcacaga tgcgtaagga gaaaataccg catcaggcgc | 8280 |
| tcttccgctt cctcgctcac tgactcgctg cgctcggtcg ttcggctgcg gcgagcggta | 8340 |
| tcagctcact caaaggcggt aatacggtta tccacagaat caggggataa cgcaggaaag | 8400 |
| aacatgtgag caaaaggcca gcaaaaggcc aggaaccgta aaaaggccgc gttgctggcg | 8460 |
| ttttccata ggctccgccc ccctgacgag catcacaaaa atcgacgctc aagtcagagg | 8520 |
| tggcgaaacc cgacaggact ataaagatac caggcgtttc ccctggaag ctccctcgtg | 8580 |
| cgctctcctg ttccgaccct gccgcttacc ggatacctgt ccgcctttct cccttcggga | 8640 |
| agcgtggcgc tttctcatag ctcacgctgt aggtatctca gttcggtgta ggtcgttcgc | 8700 |
| tccaagctgg gctgtgtgca cgaaccccc gttcagcccg accgctgcgc cttatccggt | 8760 |
| aactatcgtc ttgagtccaa cccggtaaga cacgacttat cgccactggc agcagccact | 8820 |
| ggtaacagga ttagcagagc gaggtatgta ggcggtgcta cagagttctt gaagtggtgg | 8880 |
| cctaactacg gctacactag aaggacagta tttggtatct gcgctctgct gaagccagtt | 8940 |
| accttcggaa aaagagttgg tagctcttga tccggcaaac aaaccaccgc tggtagcggt | 9000 |
| ggttttttg tttgcaagca gcagattacg cgcagaaaaa aaggatctca agaagatcct | 9060 |
| ttgatctttt ctacggggtc tgacgctcag tggaacgaaa actcacgtta agggattttg | 9120 |
| gtcatgaaca ataaaactgt ctgcttacat aaacagtaat acaaggggtg ttatgagcca | 9180 |
| tattcaacgg gaaacgtctt gctcgaggcc gcgattaaat tccaacatgg atgctgattt | 9240 |
| atatgggtat aaatgggctc gcgataatgt cgggcaatca ggtgcgacaa tctatcgatt | 9300 |
| gtatgggaag cccgatgcgc cagagttgtt tctgaaacat ggcaaaggta gcgttgccaa | 9360 |
| tgatgttaca gatgagatgg tcagactaaa ctggctgacg gaatttatgc ctcttccgac | 9420 |
| catcaagcat tttatccgta ctcctgatga tgcatggtta ctcaccactg cgatccccgg | 9480 |
| gaaaacagca ttccaggtat tagaagaata tcctgattca ggtgaaaata ttgttgatgc | 9540 |
| gctggcagtg ttcctgcgcc ggttgcattc gattcctgtt tgtaattgtc cttttaacag | 9600 |
| cgatcgcgta tttcgtctcg ctcaggcgca atcacgaatg aataacggtt tggttgatgc | 9660 |
| gagtgatttt gatgacgagc gtaatggctg gcctgttgaa caagtctgga agaaatgca | 9720 |
| taagcttttg ccattctcac cggattcagt cgtcactcat ggtgatttct cacttgataa | 9780 |
| ccttattttt gacgagggga aattaatagg ttgtattgat gttggacgag tcggaatcgc | 9840 |
| agaccgatac caggatcttg ccatcctatg gaactgcctc ggtgagtttt ctccttcatt | 9900 |
| acagaaacgg ctttttcaaa aatatggtat tgataatcct gatatgaata aattgcagtt | 9960 |
| tcatttgatg ctcgatgagt ttttctaaga attc | 9994 |

<210> SEQ ID NO 2
<211> LENGTH: 4981
<212> TYPE: DNA
<213> ORGANISM: Artificial Sequence
<220> FEATURE:
<223> OTHER INFORMATION: Simian immunodeficiency virus/human
      immunodeficiency virus

<400> SEQUENCE: 2

| | |
|---|---|
| cgcccgaaca gggacttgaa ggagagtgag agactcctga gtacggctga gtgaaggcag | 60 |
| taagggcggc aggaaccaac cacgacggag tgctcctata aaggcgcggg tcggtaccag | 120 |

```
acggcgtgag gagcgggaga ggaagaggcc tccggttgca ggtgagtgca acacaaaaaa    180
gaaatagctg tcttttatcc aggaaggggt aataagatag agtgggagat gggcgtgaga    240
aactccgtct tgtcagggaa gaaagcagat gaattagaaa aaattaggct acgacccaac    300
ggaaagaaaa agtacatgtt gaagcatgta gtatgggcag caaatgaatt agatagattt    360
ggattagcag aaagcctgtt ggagaacaaa gaaggatgtc aaaaaatact ttcggtctta    420
gctccattag tgccaacagg ctcagaaaat ttaaaaagcc tttataatac tgtctgcgtc    480
atctggtgca ttcacgcaga agagaaagtg aaacacactg aggaagcaaa acagatagtg    540
cagagacacc tagtggtgga ataggaacaa cagaaactgt gccaaaaac aagtagacca     600
acagcaccat ctagcggcag aggaggaaat tacccagtac aacaaatagg tggtaactat    660
gtccacctgc cattaagccc gagaacatta aatgcctggg taaaattgat agaggaaaag    720
aaatttggag cagaagtagt gccaggattt caggcactgt cagaaggttg caccccctat    780
gacattaatc agatgttaaa ttgtgtggga gaccatcaag cggctatgca gattatcaga    840
gatattataa acgaggaggc tgcagattgg gacttgcagc acccacaacc agctccacaa    900
caaggacaac ttagggagcc gtcaggatca gatattgcag gaacaactag ttcagtagat    960
gaacaaatcc agtggatgta cagacaacag acccccatac cagtaggcaa catttacagg   1020
agatggatcc aactgggggtt gcaaaaatgt gtcagaatgt ataacccaac aaacattcta   1080
gatgtaaaac aaggggccaaa agagccattt cagagctatg tagacaggtt ctacaaaagt   1140
ttaagagcag aacagacaga tgcagcagta agaattgga tgactcaaac actgctgatt    1200
caaaatgcta acccagattg caagctagtg ctgaagggc tgggtgtgaa tcccaccta     1260
gaagaaatgc tgacggcttg tcaaggagta gggggggccgg gacagaaggc tagattaatg   1320
gcagaagccc tgaaagaggc cctcgcacca gtgcctatcc cttttgcagc agcccaacag   1380
aggggaccaa gaaagccaat taagtgttgg aattgtggga agagggaca ctctgcaagg    1440
caatgcagag ccccaagaag acagggatgc tggaaatgtg gaaaaatgga ccatgttatg   1500
gccaaatgcc cagacagaca ggcgggtttt ttaggccttg gtccatgggg aaagaagccc   1560
cgcaatttcc ccatggctca agtgcatcag gggctgatgc caactgctcc cccagaggac   1620
ccagctgtgg atctgctaaa gaactacatg cagttgggca agcagcagag agaaaagcag   1680
agagaaagca gagagaagcc ttacaaggag gtgacagagg attttgctgca cctcaattct   1740
ctctttggag gagaccagta gtcactgctc atattgaagg acagcctgta gaagtattac   1800
tggatacagg ggctgatgat tctattgtaa caggaataga gttaggtcca cattatacccc  1860
caaaaatagt aggaggaata ggaggttttta ttaatactaa agaatacaaa aatgtagaaa   1920
tagaagtttt aggcaaaagg attaaaggga caatcatgac aggggacacc ccgattaaca   1980
ttttggtag aaatttgcta acagctctgg ggatgtctct aaattttccc atagctaaag    2040
tagagcctgt aaaagtcgcc ttaaagccag gaaagaatgg accaaaattg aagcagtggc   2100
cattatcaaa agaaaagata gttgcattaa agaaatctg gaaaagatg gaaaggatg      2160
gtcagttgga ggaagctccc ccgaccaatc catacaacac ccccacattt gctataaaga   2220
aaaaggataa gaacaaatgg agaatgctga tagattttag gaactaaat agggtcactc    2280
aggactttac ggaagtccaa ttaggaatac cacaccctgc aggattagca aaaggaaaa    2340
gaattacagt actggatata ggtgatgcat atttctccat acctctagat gaagaattta   2400
ggcagtacac tgcctttact ttaccatcag taaataatgc agagccagga aaacgataca   2460
tttataaggt tctgcctcag ggatggaagg ggtcaccagc catcttccaa tacactatga   2520
```

```
gacatgtgct agaacccttc aggaaggcaa atccagatgt gaccttagtc cagtatatgg    2580
atgacatctt aatagctagt gacaggacag acctggaaca tgacagggta gttttacagt    2640
caaaggaact cttgaatagc atagggtttt ctaccccaga agagaaattc caaaaagatc    2700
ccccatttca atggatgggg tacgaattgt ggccaacaaa atggaagttg caaaagatag    2760
agttgccaca aagagagacc tggacagtga atgatataca gaagttagta ggagtattaa    2820
attgggcagc tcaaatttat ccaggtataa aaccaaaca tctctgtagg ttaattagag    2880
gaaaaatgac tctaacagag gaagttcagt ggactgagat ggcagaagca gaatatgagg    2940
aaaataaaat aattctcagt caggaacaag aaggatgtta ttaccaagaa ggcaagccat    3000
tagaagccac ggtaataaag agtcaggaca atcagtggtc ttataaaatt caccaagaag    3060
acaaaatact gaaagtagga aaatttgcaa agataaagaa tacacatacc aatggagtga    3120
gactattagc acatgtaata cagaaaatag gaaaggaagc aatagtgatc tggggacagg    3180
tcccaaaatt ccacttacca gttgagaagg atgtatggga acagtggtgg acagactatt    3240
ggcaggtaac ctggataccg gaatgggatt ttatctcaac accaccgcta gtaagattag    3300
tcttcaatct agtgaaggac cctatagagg gagaagaaac ctattataca gatggatcgt    3360
gtaataaaca gtcaaaagaa gggaaagcag gatatatcac agatagggc aaagacaaag    3420 taaaagtgtt agaacagact actaatcaac aagcagaatt ggaagcattt ctcatggcat    3480
tgacagactc agggccaaag gcaaatatta tagtagattc acaatatgtt atgggaataa    3540
taacaggatg ccctacagaa tcagagagca ggctagttaa tcaaataata gaagaaatga    3600
ttaaaaagtc agaaatttat gtagcatggg taccagcaca caaggtata ggaggaaacc    3660 aagaaataga ccacctagtt agtcaaggga ttagacaagt tctcttcttg gaaaagatag    3720
agccagcaca agaagaacat gataaatacc atagtaatgt aaaagaattg gtattcaaat    3780
ttggattacc cagaatagtg gccagacaga tagtagacac ctgtgataaa tgccatcaga    3840
aaggagaggc tatacatggg caggtaaatt cagatctagg gacttggcaa atggattgta    3900
cccatctaga gggaaaaata atcatagttg cagtacatgt agctagtgga ttcatagaag    3960
cagaggtaat tccacaagag acaggaagac agacagcact atttctgtta aaattggcag    4020
gcagatggcc tattacacat ctacacacag ataatggtgc taactttgct tcgcaagaag    4080
taaagatggt tgcatggtgg gcagggatag agcacacctt tggggtacca tacaatccac    4140
agagtcaggg agtagtggaa gcaatgaatc accacctgaa aaatcaaata gatagaatca    4200
gggaacaagc aaattcagta gaaaccatag tattaatggc agttcattgc atgaatttta    4260
aaagaagggg aggaatacgg gatatgactc cagcagaaag attaattaac atgatcacta    4320
cagaacaaga gatacaattt caacaatcaa aaaactcaaa atttaaaaat tttcgggtct    4380
attacagaga aggcagagat caactgtgga agggacccgg tgagctattg tggaaagggg    4440
aaggagcagt catcttaaag gtaggacag acattaaggt agtacccaga agaaaggcta    4500
aaattatcaa agattatgga ggaggaaaag aggtggatag cagttcccac atggaggata    4560
ccggagaggt tagagaggtg gcatagcctc ataaaatatc tgaaatataa aactaaagat    4620
ctacaaaagg tttgctatgt gccccatttt aaggtcggat gggcatggtg gacctgcagc    4680
agagtaatct tcccactaca ggaaggaagc catttagaag tacaagggta ttggcatttg    4740
acaccagaaa aagggtggct cagtacttat gcagtgagga taacctggta ctcaaagaac    4800
ttttggacag atgtaacacc aaactatgca gacattttac tgcatagcac ttatttccct    4860
```

| tgctttacag cgggagaagt gagaagggcc atcaggggag aacaactgct gtcttgctgc | 4920 |
| aggttcccga gagctcataa gcaccaggta ccaagcctac agtacttagc actgaaagta | 4980 |
| g | 4981 |

<210> SEQ ID NO 3
<211> LENGTH: 472
<212> TYPE: DNA
<213> ORGANISM: Artificial Sequence
<220> FEATURE:
<223> OTHER INFORMATION: Simian immunodeficiency virus/human
      immunodeficiency virus

<400> SEQUENCE: 3

| atggaggagg aaaagaggtg gatagcagtt cccacatgga ggataccgga gaggttagag | 60 |
| aggtggcata gcctcataaa atatctgaaa tataaaacta agatctcaca aaaggtttgc | 120 |
| tatgtgcccc attttaaggt cggatgggca tggtggacct gcagcagagt aatcttccca | 180 |
| ctacaggaag gaagccattt agaagtacaa gggtattggc atttgacacc agaaaaaggg | 240 |
| tggctcagta cttatgcagt gaggataacc tggtactcaa gaacttttg acagatgta | 300 |
| acaccaaact atgcagacat tttactgcat agcacttatt tcccttgctt tacagcggga | 360 |
| gaagtgagaa gggccatcag gggagaacaa ctgctgtctt gctgcaggtt cccgagagct | 420 |
| cataagcacc aggtaccaag cctacagtac ttagcactga agtagtaag cg | 472 |

<210> SEQ ID NO 4
<211> LENGTH: 2376
<212> TYPE: DNA
<213> ORGANISM: Human immunodeficiency virus

<400> SEQUENCE: 4

| cgcccgaaca gggacgcgaa agcgaaagta gaaccagagg agctctctcg acgcaggact | 60 |
| cggcttgctg aagcgcgcac ggcaagaggc gaggggcggc gactggtgag tacgccattt | 120 |
| ttgactagcg gaggctagaa ggagagagat gggtgcgaga gcgtcaatat taagcggggg | 180 |
| acaattagat agatgggaaa aaattcggtt acggccaggg ggaaagaaaa gatataagtt | 240 |
| aaaacatata gtatgggcaa gcagagagct agaacgattc gcagttaacc ctggcctgtt | 300 |
| agaaacagca aaggctgta gacaaatact gggacagcta caaccatccc ttcagacagg | 360 |
| atcagaggaa cttaaatcat tatttaatac aatagctacc ctctattgtg tacatcaaag | 420 |
| aatagagata aaagacacca aggaagcttt agataagata gaggaagagc aaaacaaaag | 480 |
| taagaaaaaa gcacagcaag cagcagctga cacaggaaac agcagcagcc aagtcagcca | 540 |
| aaattaccct atagtgcaga acgctcaggg acaaatggta catcaggcca tatcacctag | 600 |
| aactttaaat gcatgggtaa agtagtaga agaaaaggct tttaacccag aagtaatacc | 660 |
| catgttttca gcattgtcag aaggagccac cccacaagat ttaaacacca tgctaaacac | 720 |
| agtgggggga catcaagcag ccatgcaaat attaaaagag actatcaatg aggaagctgc | 780 |
| agaatgggat agattgcatc cagtacatgc agggcctatt gcaccaggcc aaatgagaga | 840 |
| accaagggga agtgacatag caggaactac tagtacccct caggaacaaa taggatggat | 900 |
| gacaaataat ccacctatcc cagtaggaga atctataaa aaatggataa tcatgggatt | 960 |
| aaataaaatt gtaaggatgt atagccctac cagtattctg gacataagac aaggaccaaa | 1020 |
| ggaacccttt agagactatg tagaccggtt ctataaaact ctaagagccg agcaagcttc | 1080 |
| acaggaagta aaaaattgga tgacagaaac cttgttggtc caaaattcaa accccgattg | 1140 |

```
taagactatt ttaaaagcat taggaccagg agctacacta gaagaaatga tgacagcatg    1200
ccagggagtg ggaggacctg gccataaagc aagagttttg gcagaagcaa tgagccaagt    1260
aacaaatcca acggccgtga tgatgcagaa aagcaatttt aggggccaaa gaaaaattgt    1320
taagtgtttt aattgtggca agaagggca catagccaaa aattgcaggg ctcctagaaa     1380
aaagggctgt tggaaatgtg gaaggaagg acaccaaatg aaagattgta ctgaaagaca     1440
ggctaatttt ttagggaaga tctggccttc ctacaaggga aggccaggga attttcctca    1500
aagcaggcta gaaccaacag ccccaccaga agcgagcttc aggtttgggg aggagacaac    1560
aactccccct cagaagcagg agacgataga caaggaggtg tatcctttaa cctccctcag    1620
atcactcttt ggcaacgacc cctcgtcaca ataaagatag gggggcaact aaaagaagct    1680
ctattagata caggagcaga tgatacagtg ttagaagaca tgaatttgcc aggaaaatgg    1740
aaaccaaaaa tgatagggg aattggagga tttatcaaag taaaacagta tgatcagata    1800
cccatagaaa tctgtggaca taaaactata ggtacagtat taataggacc tacacctgtc    1860
aacataattg gaaggaattt gttgactcag cttggttgca ctttaaattt tcccattagt    1920
cctattgaaa ctgtaccagt aaaattaaag ccaggaatgg atggcccaaa agttaagcaa    1980
tggccattga cagaagaaaa aataaaagca ttaatggaga tatgcacaga aatggaaaag    2040
gaagggaaaa tttcaaaaat tgggcctgaa aatccataca atactccagt gtttgccata    2100
aagaaaaaag acagtactaa gtggagaaaa ttagtagatt tcagagaact taataagaaa    2160
actcaagact tctgggaggt tcaattagga ataccacatc ccgcggggtt aaaaaagaaa    2220
aagtcagtaa cagtactgga tgtgggtgat gcatacttct cagttccctt agatgaagat    2280
tttaggaagt atactgcatt taccataccc agtataaaca atgagacatc aggaattaga    2340
tatcagtaca atgtgcttcc acagggatgg aaaggg                              2376
```

<210> SEQ ID NO 5
<211> LENGTH: 411
<212> TYPE: DNA
<213> ORGANISM: Human immunodeficiency virus

<400> SEQUENCE: 5

```
aacagcaggg actttccaca aggggatgtt acggggaggt actggggagg agccggtcgg    60
gaacgcccac tttcttgatg tataaatatc actgcatttc gctctgtatt cagtcgctct    120
gcggagaggc tggcaggttg agccctggga ggttctctcc agcactagca ggtagagcct    180
gggtgttccc tgctagactc tcaccagcac ttggccggtg ctgggcagag tgattccacg    240
cttgcttgct taaagccctc ttcaataaag ctgccatttt agaagtaagc tagtgtgtgt    300
tcccatctct cctagccgcc gcctggtcaa ctcggtactc aataataaga agaccctggt    360
ctgttaggac cctttctgct ttgggaaacc gaagcaggaa aatccctagc a             411
```

<210> SEQ ID NO 6
<211> LENGTH: 481
<212> TYPE: DNA
<213> ORGANISM: SV40

<400> SEQUENCE: 6

```
tcgagggggg gcccggtacc ttaattaatt aaggtaccag gtaagtgtac ccaattcgcc    60
ctatagtgag tcgtattaca attcactcga tcgcccttcc caacagttgc gcagcctgaa    120
tggcgaatgg agatccaatt tttaagtgta taatgtgtta aactactgat tctaattgtt    180
tgtgtatttt agattcacag tcccaaggct catttcaggc ccctcagtcc tcacagtctg    240
```

```
ttcatgatca taatcagcca taccacattt gtagaggttt tacttgcttt aaaaaacctc      300
ccacacctcc ccctgaacct gaaacataaa atgaatgcaa ttgttgttgt taacttgttt      360
attgcagctt ataatggtta caaataaagc aatagcatca caaatttcac aaataaagca      420 ttttttcac tgcattctag ttgtggtttg tccaaactca tcaatgtatc ttaacgcgta       480
a                                                                      481

<210> SEQ ID NO 7
<211> LENGTH: 818
<212> TYPE: DNA
<213> ORGANISM: Simian immunodeficiency virus

<400> SEQUENCE: 7
tggaagggat ttattacagt gcaagaagac atagaatctt agacatgtac ttagaaaagg       60
aaaaaggcat cataccagat tggcaggatt acacctcagg accaggaatt agatacccaa      120
agacatttgg ctggctatgg aaattagtcc ctgtaaatgt atcagatgag gcacaggagg      180
atgaagagca ttatttaatg catccagctc aaacttccca gtgggatgac ccttggagag      240
aggttctagc atggaagttt gatccaactc tggcctacac ttatgaggca tatgttagat      300
acccagaaga gtttggaagc aagtcaggcc tgtcagagga agaggttaaa agaaggctaa      360
ccgcaagagg ccttcttaac atggctgaca agaaggaaac tcgctgaaac agcagggact      420
ttccacaagg ggatgttacg gggaggtact ggggaggagc cggtcgggaa cgcccacttt      480
cttgatgtat aaatatcact gcatttcgct ctgtattcag tcgctctgcg gagaggctgg      540
caggttgagc cctgggaggt tctctccagc actagcaggt agagcctggg tgttccctgc      600
tagactctca ccagcacttg gccggtgctg ggcagagtga ttccacgctt gcttgcttaa      660
agccctcttc aataaagctg ccattttaga agtaagctag tgtgtgttcc catctctcct      720
agccgccgcc tggtcaactc ggtactcaat aataagaaga ccctggtctg ttaggaccct      780
ttctgctttg ggaaaccgaa gcaggaaaat ccctagca                              818
```

DNA VACCINE COMPOSITIONS WITH HIV/SIV GENE MODIFICATIONS

CROSS-REFERENCE TO RELATED APPLICATION

The application claims benefit of U.S. Provisional Application No. 60/503,197, filed Sep. 16, 2003; U.S. patent application Ser. No. 12/368,151, filed Feb. 9, 2009; and U.S. Pat. No. 7,488,485, filed Sep. 15, 2004. This application is a continuation of U.S. patent application Ser. No. 12/368,151.

STATEMENT OF GOVERNMENT RIGHTS

This work was supported in part by NIH grant numbers G1401830 and G1402500. The government of the United States of America may have rights in this invention.

FIELD OF INVENTION

The present invention relates generally to the field of prophylactic vaccines for generating protection from HIV-1 induced disease and infection. More specifically, the present invention relates to DNA vaccines against the Human Immunodeficiency Virus (HIV).

BACKGROUND OF INVENTION

By the end of the year 2000, an estimated 36.1 million people worldwide were infected with HIV. In that year alone, HIV/AIDS-associated illnesses claimed the lives of approximately 3 million people worldwide. An estimated 500,000 of those deaths were of children under the age of fifteen. The importance of an HIV vaccine with respect to world health cannot be overstated.

It is recognized that effective vaccines that will inhibit or prevent HIV-1 infection or HIV-1 induced disease in humans will be useful for the treatment of certain high-risk populations, and as a general prophylactic vaccination for the general population that may risk HIV-1 infection or HIV-1 induced disease. A vaccine that will confer long-term protection against the transmission of HIV-1 would be most useful. Unfortunately, numerous problems stand in the way of developing effective vaccines for the prevention of HIV-1 infection and disease. Certain problems are most likely the result of the unique nature of the HIV-1 virus and its functional properties, and as yet no effective vaccine has been developed (for review, see: Berzofsky et al., Developing Synthetic Peptide Vaccines for HIV-1, *Vaccines* 95, pps. 135-142, 1995; Cease and Berzofsky, Toward a Vaccine for AIDS: The Emergence of Immunobiology¬Based Vaccine Design, *Annual Review of Immunology*, 12:923-989; Berzofsky, Progress Toward Artificial Vaccines for HIV, *Vaccines* 92, pps. 40-41, 1992).

HIV is a retrovirus, meaning that its genome consists of RNA rather than DNA. There are two primary strains of the virus, designated HIV-1 and HIV-2, with HIV-1 being the strain that is primarily responsible for human infection. The RNA genome of HIV is surrounded by a protein shell. The combination of RNA genome and the protein shell is known as the nucleocapsid, which is in turn surrounded by an envelope of both protein and lipid.

Infection of host cells by HIV begins when the gp120 protein of HIV, a highly glycosylated protein located in the viral envelope, binds to the CD4 receptor molecule of a host cell. This interaction initiates a series of events that allow fusion between the viral and cell membranes and the subsequent entry of the virus into the cell.

Following entry into the host cell, HIV RNA is transcribed into double-stranded DNA by a viral reverse transcriptase enzyme. Once integrated into the host genome, HIV expresses itself through transcription by the host's RNA Polymerase II enzyme. Through both transcriptional control and posttranscriptional transcript processing, HIV is able to exert a high level of control over the extent to which it expresses itself Studies of the HIV virus have revealed much information about the molecular biology of the virus, including information concerning a number of genes and genetic regions important to the pathogenicity of HIV. Among these important genes and regions are rt, int, vif, and the 3' LTR of HIV.

The rt gene of HIV encodes viral reverse transcriptase. This enzyme utilizes the RNA genome of HIV to produce a corresponding linear double-stranded DNA molecule that can be incorporated into the host genome.

The int gene of HIV encodes an integrase. This is the enzyme that actually catalyzes the insertion of the reverse-transcriptase-produced linear double-stranded viral DNA into the host genome. In order to complete integration of the viral DNA into the host genome, the host cell DNA repair machinery performs a ligation of the host and viral DNAs.

The vif gene of HIV encodes a protein known as the 'viral infectivity factor.' This protein is required for the production of infectious virions. The protein likely overcomes a cellular inhibitor that otherwise inhibits HIV-1, and may also enhance the stability of the viral core and the preintegration complex.

The LTR (Long Terminal Repeat) regions of HIV-1 contain promoter regions necessary to drive expression of the HIV genes. The 5' LTR of HIV-1 contains the promoter that is primarily responsible for driving HIV-1 gene expression, though if the 5' LTR sequence is disrupted, the 3' LTR may assume this function. The 3' LTR is necessary for integration of the viral DNA into the host genome.

Among other important HIV-1 genes are gag, pol, nef, and vpu.

The gag gene encodes for, among other things, the p27 capsid protein of HIV. This protein is important in the assembly of viral nucleocapsids. The p27 protein is also known to interact with the HIV cellular protein CyA, which is necessary for viral infectivity. Disruption of the interaction between p27 and CyA has been shown to inhibit viral replication.

The pol gene contains the rt and int sequences of HIV-1, thus encoding, among other things, reverse transcriptase and integrase.

The nef gene product (known as Negative Factor, or Nef) has a number of potentially important properties. Nef has the ability to downregulate CD4 and MHC Class I proteins, both of which are important to the body's ability to recognize virus-infected cells. Nef has also been shown to activate cellular protein kinases, thereby interfering with the signaling processes of the cell. Perhaps most importantly, deletion of nef from a pathogenic clone of Simian Immunodeficiency Virus (SIV) renders the virus nonpathogenic in adult macaque monkeys. Thus, a functional nef gene is crucial for the ability of SIV to cause disease in vivo. Further, studies have shown that HIV positive individuals with large deletions in the nef gene remained healthy for well over ten years, with no reduction in cellular CD4 counts.

The vpu gene encodes a protein of originally unknown function (known as Viral Protein, Unknown, or Vpu), but which is now known to downregulate CD4 and MHC Class-I expression as well as promote viral budding. Vpu is also similar to another viral protein that acts as an ion channel. The vpu gene is present in HIV-1, but is absent in HIV-2.

In nearly all viral infections, certain segments of the infected population recover and become immune to future viral infection by the same pathogen. Examples of typical viral pathogens include measles, poliomyelitis, chicken pox, hepatitis B, and small pox. The high mortality rate of HIV-1 infection, and the extremely rare incidence of recovery and protective immunity against HIV-1 infection, has cast doubt on the ability of primates to generate natural immunity to HIV-1 infection when pathogenic HIV-1 is the unmodified wild-type viral pathogen. Thus, there is a great need for a vaccine that will confer upon primate populations protective immunity against HIV-1 virus.

A hallmark of resistance to future viral infection is the generation of 'neutralizing antibodies' capable of recognizing the viral pathogen. Another measure is cellular immunity against infected cells. In typical viral infections, generation of neutralizing antibodies and cellular immunity heralds recovery from infection. In HIV-1 infection, however, neutralizing antibodies and cellular immunity appear very early during the infection and have been associated with only a transient decrease in viral burden. In spite of the generation of neutralizing antibodies and cellular immunity, viral replication in HIV-1 infection rebounds and AIDS (acquired immune deficiency syndrome) develops. Thus, in HIV-1 infection, neutralizing antibodies and cellular immunity are not accurate measures of protective immunity.

A further problem in developing an effective vaccine for HIV-1 is the antigenic diversity of the wild-type virus. There is a strong possibility that vaccines generated via recombinant HIV-1 coat proteins will confer resistance to specific phenotypes of virus and not broad spectrum immunity. Vaccine development using recombinant HIV-1 gp120 peptide, a HIV-1 viral coat protein, has passed phase-one clinical trials showing no toxicity. Data has indicated, however, that neutralizing antibodies appeared only transiently. Thus, recombinant HIV-1 gp120-peptide vaccines may act only in the short-term, with reversion to susceptibility of infection occurring in the future.

In general, it is accepted that live-virus vaccines induce better immunity against pathogenic viruses than isolated viral proteins (see, for example, Putkonen et al., Immunization with Live Attenuated $SIV_{mac}$ Can Protect Macaques Against Mucosal Infection with $SIV_{sm}$, Vaccines 96, pps. 200-210, 1996; Dimmock and Primrose Introduction to Modern Virology, Fourth Ed., Blackwell Science, 1994). The use of live lentivirus vaccines, such as HIV-1 vaccine, is resisted because of great concern that the virus will persist indefinitely in the inoculated population because of integration of the viral DNA into the host DNA of the inoculated individuals (see, for example, Haaft et al., Evidence of Circulating Pathogenic SIV Following Challenge of Macaques Vaccinated with Live Attenuated SIV, Vaccines 96, pps. 219¬224, 1996). Thus, a safe and effective vaccine against HIV-1 will encompass modifications to prevent the development of virulent pathogenic infection that could occur by either random mutation or other change to the initially non-pathogenic vaccine virus. One possibility for such a vaccine could come in the form of a DNA vaccine against HIV-1.

DNA vaccines are generally injected into host tissues in the form of plasmid DNA or RNA molecules via needle or particle bombardment. Once delivered, the DNA induces expression of antigenic proteins within transfected cells. U.S. Pat. No. 6,194,389 describes methods for transferring DNA to vertebrate cells to produce physiological immune-response producing protein in an animal subject and is incorporated herein in its entirety by reference.

Testing of vaccine efficacy generally requires the challenge of a subject with live virus or DNA. It is ethically and practically difficult to attempt preliminary studies using human subjects. The use of model systems for preliminary design and testing of candidate vaccines has been hampered by various species-specific features of the virus. The HIV-1 virus itself is currently known only to infect certain rate and endangered species of chimpanzees in addition to humans. The feasibility of obtaining sufficient numbers of such endangered animals for full preliminary study of HIV-1 virus vaccines is quite low. It is preferable to use validated analogous animal model systems.

One analogous model system for HIV-1 has been the $SIV_{mac}$ (Simian Immunodeficiency Virus, macaque) system. SIV infects a variety of simians, including macaques, but the differences between SIV and HIV make SIV of limited use as a potential human vaccine. There is, therefore, a need for a vaccine made from a virus that is closely related to HIV, but still infectious in an animal model for purposes of testing.

Chimeric SIV-HIV virus has been developed by placing the envelope proteins of HIV-1 on a background of $SIV_{mac}$. The chimeric virus proved to be infectious in monkeys, but did not result in full-blown AIDS or an accurate model to mimic HIV-1 infection monkeys.

As described below, the present invention teaches specific DNA constructs and methods that are effective in generating an immune response to HIV-1 in a vaccinated host.

SUMMARY OF INVENTION

The present invention is directed to a DNA vaccine for immunization against HIV. The invention comprises a DNA molecule that has a sequence encoding a plurality of viral proteins capable of stimulating an immune response against HIV. The DNA molecule is rendered safe for use as a vaccine by the disruption of genes encoding reverse transcriptase, integrase, and Vif. The DNA molecule is further rendered safe by at least a partial deletion of the 3' LTR.

The DNA molecule of the present invention further includes an SV40 polyadenylation sequence. In addition, the DNA molecule of the present invention is preferably regulated by a natural SIV promoter sequence.

The present invention is also directed to a method of immunizing an individual against HIV by administering the present DNA vaccine to said individual.

The present invention is further directed toward a vaccine against multiple HIV subtypes as well as viruses other than HIV, said vaccine produced by substituting genes from said other viruses for the orthologous HIV and/or SIV genes described herein.

DETAILED DESCRIPTION

The object of the present invention is to provide DNA vaccine compositions and methods that provide either protective immunity to uninfected subjects or therapeutic immunity to infected subjects.

One aspect of the present invention is directed to DNA molecules that encode viral proteins capable of stimulating an immune response against HIV. In preferred embodiments, the DNA vaccine encodes the gag, pro, vpx, vpr, nef, tat proteins of HIV or SIV.

Importantly, the DNA molecules of the present invention have been disrupted functionally such that the ability to encode proteins that are important in pathogenicity are removed. More specifically, preferred embodiments functionally disrupt the vif, int and rt genes of the DNA vaccine. Other embodiments functionally disrupt the rt gene. It is anticipated that the DNA can be disrupted functionally by inserting or deleting at least one nucleotide such that the number of nucleotides in the altered sequences differs with respect to the unaltered sequences. It is also anticipated that the DNA encoding pathogenicity-related proteins can be disrupted functionally by substituting one or more nucleotides that encode functional amino acids with one or more distinct nucleotides that encode non-functional amino acids. In a preferred embodiment of the present invention, the functional disruption of the DNA encoding pathogenicity-related proteins occurs via deletion of the rt, int, and vif genes.

Another important aspect of this invention is that it provides for DNA vaccines that disrupt the 3' LTR sequences that enable undesirable integration of DNA sequences into the host genome. Function of the 3' LTR can also be abolished by substituting functional nucleotides with distinct non-functional nucleotides. The deleted 3' LTR region is preferably replaced with an SV40 polyadenylation sequence. Those skilled in the art will recognize that polyadenylation sites derived from a variety of sources other than SV40 may also be used as substitutes for the 3' LTR sequences.

A further aspect of the invention is the regulation of the DNA molecule of the present invention by use of the $SHIV_{ku2}$ or SIV 5'LTR promoter (SEQ ID NO:7). This promoter drives the expression of viral proteins capable of stimulating an immune response against HIV present in the DNA vaccine. Those skilled in the art will recognize that alternative embodiments of this invention may substitute other functional promoter sequences that will also drive expression of the desired viral proteins.

EXAMPLES

Example 1

Construction of the Δ4-$SHIV_{ku2}$ DNA Construct

Figure 1:
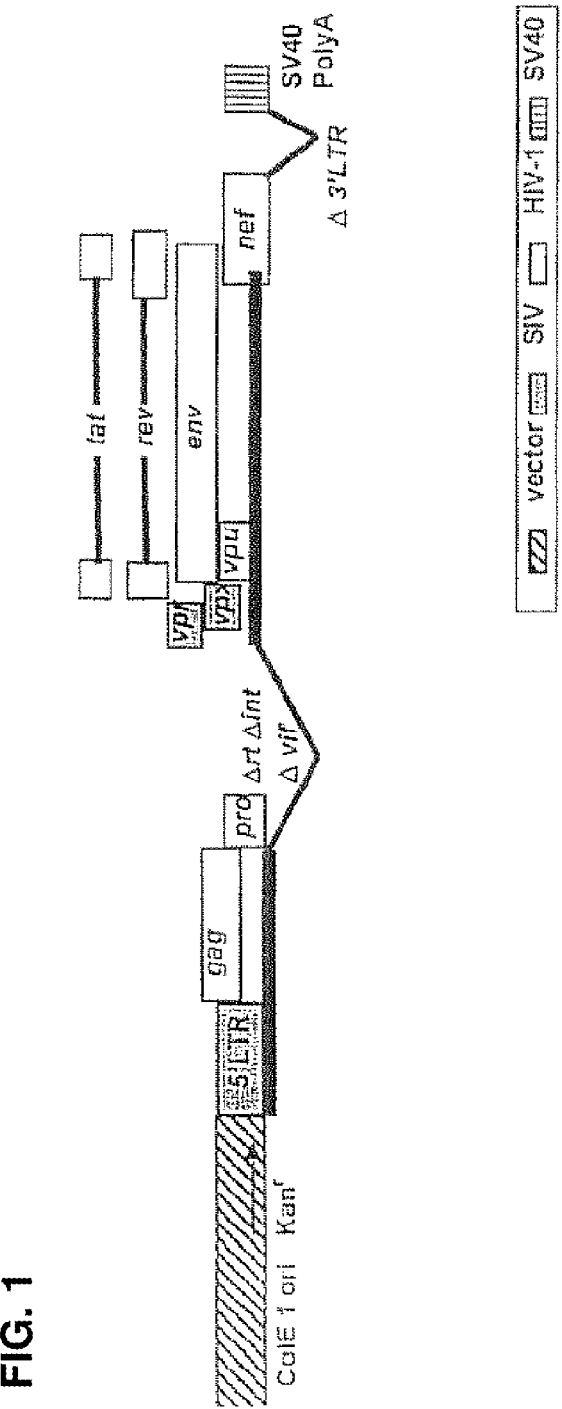
FIG. 1 is a schematic diagram of the $\Delta4$-$SHIV_{ku2}$, DNA construct of the present invention.
Figure 2:
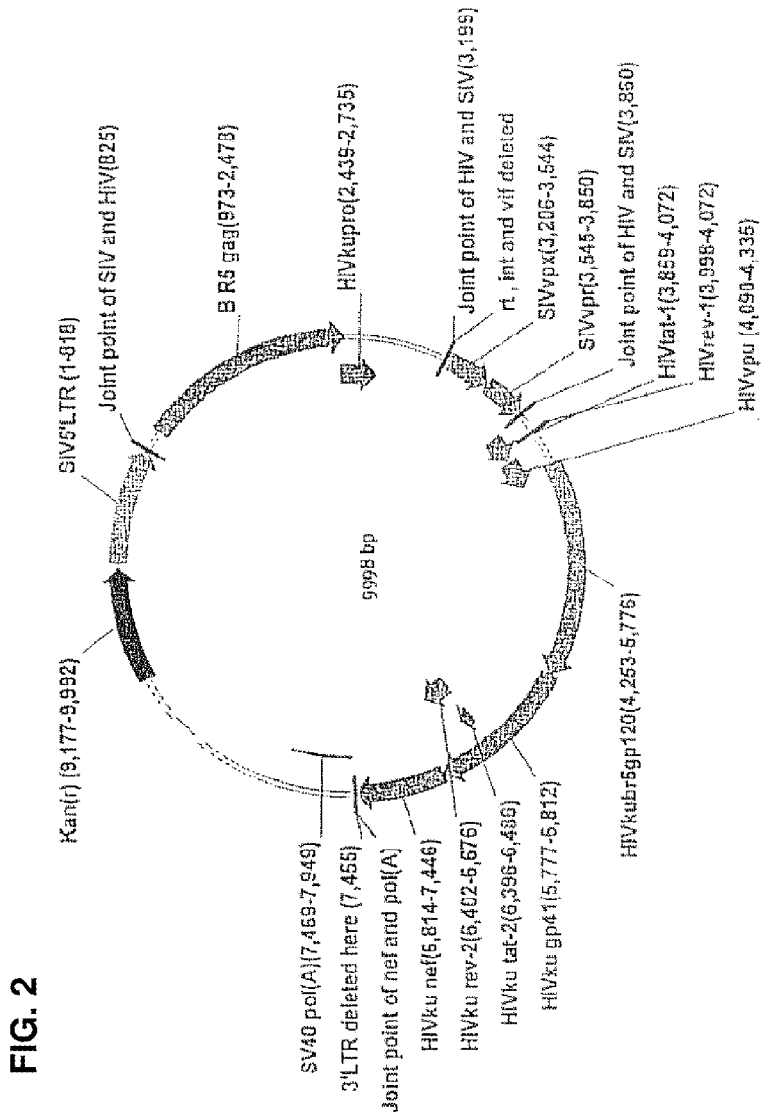
FIG. 2 is a circular diagram of the $\Delta4$-$SHIV_{ku2}$ DNA construct of the present invention.

FIG. 1 is a schematic diagram of the Δ4-$SHIV_{ku2}$ DNA construct (SEQ ID NO:1) of the present invention. The construction of the present DNA vaccine Δ4-$SHIV_{ku2}$ DNA construct (SEQ ID NO:1) is performed as follows. The vector used for the present vaccine is pET-9a. The 2.3 kb EcoR I/Xmn I fragment of pET-9a is replaced with the approximately 7.4 kb modified $SHIV_{ku2}$ provirus genome and the approximately 0.5 kb polyadenylation signal sequence of SV40 to yield an intermediate vector. EcoRI and Not I restriction sites are created immediately upstream of the 5' LTR and at the end of the nef gene, respectively, in another intermediate vector. The reverse transcriptase (rt), integrase (int), and vif genes are eliminated by deletion of an approximately 2.5 kb DNA fragment between the downstream end of the pro gene and upstream of the vpx gene. The approximately 3.8 kb nucleotide sequence that encodes the envelope (env), nef, and 3' LTR genes of $SHIV_{ku2}$ provirus genome is then replaced with the approximately 3.2 kb EcoRV/Not I DNA fragment that encodes the env and nef genes of HIV-1. The approximately 2.5 kb Nar I/BstE II DNA fragment that encodes the leader sequence, gag, and pro genes of $SIV_{mac239}$ in $SHIV_{ku2}$ is replaced with an approximately 2.4 kb Nar I/BstE II fragment that encodes the HIV-1 leader sequence, gag, and pro of HIV-1 to yield Δ4-$SHIV_{ku2}$ DNA construct (SEQ ID NO:1). Thus, the 5' LTR, vpx, and vpr genes of the present vaccine are from $SIV_{mac239}$, and the gag, pro, tat, rev, vpu, env, and nef are from HIV-1. The sequence of a preferred embodiment of the present DNA vaccine Δ4-$SHIV_{ku2}$ DNA is designated SEQ ID NO:1.

The information below is provided to detail structure of the Δ4-$SHIV_{ku2}$ DNA construct (SEQ ID NO:1) more completely. A 4,981 bp fragment of $SHIV_{ku2}$ that encodes the entire gag, and pol genes (which therefore includes the rt and int portions of the genome), as well as the first 472 by of the vif gene, is replaced with a 2,376 by DNA fragment of HIV-1 in the Δ4-$SHIV_{ku2}$ DNA construct. This 2,376 bp fragment encodes the entire HIV-1 gag gene, and a portion of the HIV-1 pal gene (the entire region encoding protease is included; the nucleotides corresponding to the first 104 amino acids of reverse transcriptase have been removed; the int and vif genes have been completely removed. The 4,981 bp fragment of $SHIV_{ku2}$ that was replaced is designated SEQ ID NO:2. The DNA sequence of the first 472 bp of the vif gene of $SHIV_{ku2}$, which was also replaced is designated SEQ ID NO:3. The DNA sequence of the 2,376 by fragment of HIV-1 used to replace the deleted 4,981 bp and 472 bp $SHIV_{ku2}$ sequences (SEQ ID NO:2 and SEQ ID NO:3, respectively) is designated SEQ ID NO:4.

In addition to the above, a 411 bp DNA fragment is deleted from the 3' LTR of $SHIV_{ku2}$ to yield the Δ4-$SHIV_{ku2}$ DNA construct (SEQ ID NO:1). This deleted 3' LTR sequence is designated SEQ ID NO:5. In the Δ4-$SHIV_{ku2}$ DNA construct the deleted 3'LTR sequences are replaced with 481 bp DNA sequence of the SV40 polyadenylation signal sequence that is designated SEQ ID NO:6.

Example 2

Efficacy of the Δ2-$SHIV_{ku2}$ DNA Vaccine

Prior to detailing the functional aspects of the present invention, and the experimental results derived from its use, it is necessary to establish the efficacy of the present invention by way of comparison with that which has come before. Prior to the invention of the present vaccine, and subsequent testing thereof, the utility thereof as a vaccine was unknown.

It is known from previous studies conducted by the inventor of the present invention that a live virus vaccine against HIV is highly efficient in eliciting protection against the virus. To establish that a DNA vaccine could be just as efficient in providing such protection, an experiment utilizing five macaques was conducted. Three of the animals were injected with a Δ2-$SHIV_{ku2}$ DNA (previously described as the V7 embodiment in patent application Ser. No. 10/279,992, herein incorporated by reference in its entirety) wherein the rt and 3' LTR had been deleted to increase the safety of the vaccine. The Δ2-$SHIV_{ku2}$ DNA also replaces the deleted 3' LTR sequence with the SV40 polyadenylation sequence. The remaining two animals were immunized with a live virus vaccine. The three animals vaccinated with the DNA vaccine were each given 2 mg of the DNA, injected intradermally, followed by an intramuscular injection of 5 mg of DNA six weeks later, and a third, 0.5 mg intramuscular DNA injection twelve weeks later. The macaques were challenged intravenously with an undiluted stock preparation of SHIV 89.6P twelve weeks after the final immunization. It is important to note that the same dose of the SERI 89.6P causes disease in 100% of inoculated control animals. The two macaques vaccinated with live virus were challenged ten weeks post-vaccination with the same SHIV virus.

When the animals were subsequently studied, it became clear that the DNA vaccine induces ELISPOT™ (Cellular Technology Limited, Cleveland, Ohio) responses against epitopes in the Env and Gag peptides, as well as neutralizing antibodies to SHIV$_{ku2}$. ELISPOT™ responses are hereby defined as measures of the number of cells expressing an indicated epitope. All three animals vaccinated with the DNA vaccine became infected with SHIV 89.6P, but each developed only low levels of viral RNA in plasma, with no loss of CD4 T-cells. The animals vaccinated with the DNA vaccine Δ2-SHIV$_{ku2}$ DNA developed a massive anamnestic ELISPOT™ response following challenge. The infection in these animals has been controlled for more than 28 weeks. At the 28-week point, the three animals that were immunized with DNA vaccine demonstrated protection that was as efficient as animals immunized with the live vaccine. Thus, the DNA vaccine proved to be just as efficient as the live vaccine in eliciting protection against heterologous SHIV 89.6P. Further, the animals receiving the DNA vaccination did not have to bear the burden of prior infection with a live vaccine virus.

Example 3

In Vivo Efficacy of Both the Δ2-SHIV$_{ku2}$ and Δ4-SHIV$_{ku2}$ DNA Vaccines

Although the experiment described in Example 2 indicated the efficacy of the DNA vaccine Δ2-SHIV$_{ku2}$ DNA lacking the rt gene and 3' LTR, it was not clear whether the current vaccine, the Δ4-SHIV$_{ku2}$, would be efficacious as a vaccine. The uncertainty stems from the fact that the current vaccine Δ4-SHIV$_{ku2}$ contains four deletions (rt, int, vif, and the 3' LTR), each deletion corresponding to a portion of the viral genome important in infectivity of the virus. The deletions were made in order to render the virus non-infectious and safe for use, but it was unknown whether these four deletions, in addition to the fact that a DNA rather than a live virus was being used, would render the vaccine incapable of providing protection against HIV-1. Surprisingly, the present virus proved to be just as efficient at inducing protection against heterologous SHIV 89.6P as the Δ2-SHIV$_{ku2}$ DNA vaccine described in the live virus comparison of Example 2.

Three macaques were injected intramuscularly with 5 mg of the Δ2-SHIV$_{ku2}$ DNA, while three other macaques were injected intramuscularly with 5 mg of the present Δ4-SHIV$_{ku2}$ DNA. The injections were repeated eleven weeks later, and the animals were challenged intravenously with undiluted stock of SHIV 89.6P six weeks after the second immunization. All six of the animals developed ELISPOT™ responses to the vaccine three weeks after the first injection, the responses declining approximately three weeks later to undetectable levels. The responses appeared once again only one week after the second injection, and again declined to low levels. Only minimal responses were detected at the time of challenge. By one week after challenge, each of the animals had developed high titers of viral replication, which were matched by a powerful CMI (cell-mediated immune) response. By two weeks post-challenge, the viral burdens in the animals declined to levels between ten- and twenty-fold less than concentrations observed one week earlier. None of the animals lost CD4 T-cells. The ability of the DNAs to induce protection after only two injections underscores the potency of the DNA vaccines, and the results of the experiment clearly showed that, despite the additional deletions, the Δ4-SHIV$_{ku2}$ DNA construct DNA vaccine (SEQ ID NO:1) of the present invention was just as effective as the Δ2-SHIV$_{ku2}$ DNA vaccine, which in turn was just as effective as the live virus vaccine.

Example 4

Utility of the SV40 Polyadenylation Sequence as a Substitute for the 3'LTR

A further experiment was performed to compare the utility of the SV40 polyadenylation sequences as substitutes for the 3' LTR sequence. This was accomplished by comparing the ability of the V5 embodiment SHIV$_{ku2}$ DNA vaccine with an intact 3'LTR and the V6 embodiment SHIV$_{ku2}$ DNA vaccine having the 3'LTR substituted with an SV40 polyadenylation sequence (SEQ ID NO: 6) to express vector-encoded viral proteins (both the V5 and V6 embodiments are described in patent application Ser. No. 10/279,992, herein incorporated by reference in its entirety). Performance of the two DNA molecules was compared in transfected primary human fibroblasts, the human embryonic kidney epithelial cell line 293, and in Jurkat cells, for expression of viral proteins in intra and extracellular compartments. The DNAs were also compared for duration of expression and for the amount of protein production, as well as for post translational modification and cleavage of precursor proteins. It was determined that the 3' LTR deleted V6 embodiment SHIV$_{ku2}$ DNA vaccine construct, surprisingly, was more efficient in producing viral proteins than the V5 embodiment SHIV$_{ku2}$ DNA vaccine construct having both LTRs. The duration of protein production was also longer in the 3' LTR deleted vaccine. Immunoprecipitation analysis revealed that deletion of the 3' LTR resulted in rapid cleavage of the gag precursor, yielding double the amount of p27 being exported to the extracellular compartment. Taken together, these data indicate that deletion of the 3' LTR not only alleviates concerns about integration of the viral genome into host DNA, but also results in a more efficient expression of viral proteins.

Example 5

Coadministration of Cytokines with Δ4-SHIV$_{ku2}$ DNA Vaccine

Next, a study was undertaken to ascertain whether the immune response induced by the present vaccine could be enhanced by co-administration of cytokines (for example, GM-CSF) DNA. BALB/C mice were immunized intramuscularly with a mixture of 100 µg of Δ4-SHIV$_{ku2}$ DNA and 25 µg of mouse GM-CSF DNA. The injections were given twice, two weeks apart, and the mice were sacrificed one week after the second immunization. Splenocytes were tested for response to SIV Gag peptides divided into five groups in the ELISPOT™ assay. Even though the immunization doses were low and tissue samples were harvested early, before CMI responses could peak, all four animals that received GM-CSF DNA along with the vaccine DNA developed ELISPOT™ responses, varying from 20 to 40 cells/$10^6$ splenocytes, whereas only 50% of the animals receiving the vaccine DNA alone developed such a response. The GM-CSF caused an impressive chemotactic effect, as evidenced by the large number of mononuclear cells that were concentrated at the site of injection. This effect attracted many more antigen-presenting dendritic cells to the site of the injection than evident in the animals that received the DNA vaccine only. Surprisingly, however, the mice that received both vaccine DNA and GM-CSF developed lower CMI titers than those receiving the DNA vaccine alone. That is, the number of viral protein specific ELISPOT™ positive cells generated by the vaccine alone was significantly higher than those generated by the vaccine plus GM-CSF. It is concluded that coadministration of the Δ4-SHIV$_{ku2}$ DNA vaccine with a cytokine such as GM-CSF may be desirable in instances where it is either prophylactically or therapeutically desirable to increase the number of injected subjects that develop activated splenocytes.

Thus, the present DNA vaccine is useful for providing protection against HIV. The DNA used in the present invention was derived from SHIV$_{ku2}$, a virus that has a highly efficient replication strategy, making it highly pathogenic. The transcriptional machinery of the DNA was maintained by preserving the 5' LTR that houses the promoter/enhancer sequences of the viral DNA. In addition, the 5' LTR contains binding sites for transcription factors such as NFKB, NFAT, SP-1, and the like, and the binding site for the RNA of tat, a molecule unique to HIV and the lentivirus that is responsible for the transactivation of viral DNA. The integrase gene and the 3' LTR were deleted to minimize the ability of the DNA to integrate into host cell DNA. Thus, the DNA cannot persist indefinitely in tissues. Furthermore, the deletion of the reverse transcriptase and vif genes crippled the ability of the genome to code for infectious virus. At the same time, the viral proteins encoded by the env, gag, vpu, tat, and nef genes were highly expressed in cells transfected with the DNA. The present DNA vaccine is highly immunogenic in macaques and elicits protective immunity against heterologous viruses. Importantly, the present vaccine can be used not only prophylactically, but also therapeutically in individuals already infected with HIV because the DNA may be injected at any time during a period when anti-retroviral drug therapy is in place.

The examples and disclosure provided above describe certain embodiments of the present invention, but are not meant to be limiting. It will be apparent to those of skill in the art, upon reading this disclosure, that the present invention may be modified in a number of ways without departing from the spirit or scope of the invention. For example, the env, gag, and nef genes described above could be excised and replaced with the corresponding genes from another subtype of HIV. Thus, the present vaccine could be used for immunization against various subtypes of HIV. Further, the env, gag, nef, and other genes described above could be replaced with genes from other viruses, such as SARS and Hepatitis C. Thus, the present DNA vaccine, described above, could be used as an 'engine' to drive expression of viral genes from other than HIV or SIV, thereby providing a DNA vaccine to a variety of other viruses. The present invention is limited only by the claims that follow.

What is claimed is:

1. A DNA composition comprising: a promoter sequence operably linked to a coding sequence, wherein the coding sequence encodes a gag gene of Human Immunodeficiency Virus (HIV), a pro gene of HIV, a vpx gene of Simian Immunodeficiency Virus (SIV), a vpr gene of SIV, a vpu gene of HIV, a nef gene of HIV, a tat gene of HIV, an env gene of HIV, and a rev gene of HIV, with the coding sequence operably linked to a polyadenylation sequence, wherein the coding sequence encodes at least one non-functional gene, wherein the DNA composition does not include functional reverse transcriptase (rt), integrase (int), and viral infectivity factor (vif) genes, and wherein the DNA composition is capable of stimulating an immune response in a recipient subject.

2. The DNA composition of claim 1, wherein the promoter sequence is a 5' long terminal repeat (LTR) of SIV.

3. The DNA composition of claim 1, wherein the DNA composition lacks a functional 3' LTR sequence.

4. The DNA composition of claim 1, wherein the polyadenylation sequence is an SV40 polyadenylation sequence.

5. The DNA composition of claim 1 further comprising a pharmaceutically acceptable carrier.

6. A pharmaceutical composition comprising:
(a) a DNA composition having a promoter sequence operably linked to a coding sequence, wherein the coding sequence encodes a gag gene of Human Immunodeficiency Virus (HIV), a pro gene of HIV, a vpx gene of Simian Immunodeficiency Virus (SIV), a vpr gene of SIV, a vpu gene of HIV, a nef gene of HIV, a tat gene of HIV, an env gene of HIV, and a rev gene of HIV, with the coding sequence operably linked to a polyadenylation sequence, and wherein the DNA composition does not include functional reverse transcriptase (rt), integrase (int), viral infectivity factor (vif) genes; and,
(b) a pharmaceutically acceptable carrier.

7. The pharmaceutical composition of claim 6, wherein the coding sequence encodes at least one non-functional gene.

8. The pharmaceutical composition of claim 6, wherein the promoter sequence is a 5' long terminal repeat (LTR) of SIV.

9. The pharmaceutical composition of claim 6, wherein the DNA composition lacks a functional 3' LTR sequence.

10. The pharmaceutical composition of claim 6, wherein the polyadenylation sequence is an SV40 polyadenylation sequence.

* * * * *